United States Patent [19]

Handke et al.

[11] Patent Number: 5,724,965
[45] Date of Patent: Mar. 10, 1998

[54] NASAL MASK

[75] Inventors: Patrick M. Handke, Monroeville; John R. Starr, Leechburg; Doris Wong, Trafford, all of Pa.

[73] Assignee: Respironics Inc., Pittsburgh, Pa.

[21] Appl. No.: 470,982

[22] Filed: Jun. 6, 1995

[51] Int. Cl.⁶ .................................................. A61M 16/06
[52] U.S. Cl. .............................. 128/207.13; 128/207.18; 128/205.25; 128/206.26
[58] Field of Search .................. 128/201.19, 207.13, 128/206.11, 206.18, 207.18, 205.25, 206.12, 206.26, 206.21, 201.22, 204.18

[56] References Cited

U.S. PATENT DOCUMENTS

| | | | |
|---|---|---|---|
| 781,516 | 1/1905 | Guthrie | 128/207.13 |
| 844,097 | 2/1907 | Caldwell | 128/203.22 |
| 938,247 | 10/1909 | Kuhn | 128/206.26 |
| 1,206,045 | 11/1916 | Smith | 128/206.24 |
| 1,635,275 | 7/1927 | Johnson | 128/200.24 |
| 2,047,216 | 7/1936 | McKesson | 128/206.26 |
| 2,241,535 | 5/1941 | Boothby et al. | 128/205.17 |
| 2,666,432 | 1/1954 | Stanton | 128/206.26 |
| 2,868,199 | 1/1959 | Hudson | 128/207.18 |
| 2,931,356 | 4/1960 | Schwarz | 128/146 |
| 3,292,618 | 12/1966 | Davis et al. | 128/201.19 |
| 3,315,674 | 4/1967 | Bloom et al. | 128/201.19 |
| 3,330,274 | 7/1967 | Bennett | 128/146.7 |
| 3,530,273 | 9/1970 | Bennett | 128/146.7 |
| 4,077,404 | 3/1978 | Elam | 128/145.8 |
| 4,151,843 | 5/1979 | Brekke et al. | 128/203 |
| 4,156,426 | 5/1979 | Gold | 128/205 |
| 4,266,540 | 5/1981 | Panzik et al. | 128/207.13 |
| 4,354,488 | 10/1982 | Bartos | 128/205.25 |
| 4,414,973 | 11/1983 | Matheson et al. | 128/206.15 |
| 4,452,240 | 6/1984 | Moretti | 128/201.18 |
| 4,454,880 | 6/1984 | Muto et al. | 128/205.25 |
| 4,559,940 | 12/1985 | McGinnis | 128/206.26 |
| 4,574,799 | 3/1986 | Warncke | 128/206.24 |
| 4,655,213 | 4/1987 | Rapoport et al. | 128/205.25 |
| 4,770,169 | 9/1988 | Schmoeener et al. | 128/207.18 |
| 4,782,832 | 11/1988 | Trimble et al. | 128/207.18 |
| 4,856,508 | 8/1989 | Tayebi | 128/206.12 |
| 4,905,683 | 3/1990 | Cronjaeger | 128/202.22 |
| 4,907,584 | 3/1990 | McGinnis | 128/206.24 |
| 4,919,128 | 4/1990 | Kopala et al. | 128/207 |
| 4,926,853 | 5/1990 | Mennier | 128/201.18 |
| 4,944,310 | 7/1990 | Sullivan | 128/848 |
| 4,945,907 | 8/1990 | Tayebi | 128/206.12 |
| 4,957,106 | 9/1990 | Vandeputte | 128/201.19 |
| 4,960,121 | 10/1990 | Nelson et al. | 128/206.24 |
| 4,961,420 | 10/1990 | Cappa et al. | 128/201.19 |
| 4,971,051 | 11/1990 | Toffolon | 128/206.26 |
| 5,042,478 | 8/1991 | Kopala et al. | 128/207.18 |
| 5,080,094 | 1/1992 | Tayebi | 128/205.29 |
| 5,094,236 | 3/1992 | Tayebi | 128/206.12 |
| 5,181,506 | 1/1993 | Tardiff, Jr. et al. | 128/211.22 |
| 5,243,971 | 9/1993 | Sullivan et al. | 128/205.25 |
| 5,355,878 | 10/1994 | Griffiths et al. | 128/205.25 |
| 5,526,806 | 6/1996 | Sansoni | 128/206.11 |
| 5,560,354 | 10/1996 | Berthon-Jones et al. | 128/204.18 |

FOREIGN PATENT DOCUMENTS 27600 of 1903 United Kingdom ............... 128/207.13

Primary Examiner—Edgar S. Burr
Assistant Examiner—Daniel J. Colilla
Attorney, Agent, or Firm—J. Stewart Brams

[57] ABSTRACT

A miniature nasal mask for supplying breathing gas to a human user through an interface with the user's nares, the interface being maintained by a contact seal which engages the user's face only within an area between the tip and immediately adjacent lateral flanks of the user's nose adjacent to the nares, and the user's upper lip.

10 Claims, 6 Drawing Sheets

5,724,965

NASAL MASK

BACKGROUND OF THE INVENTION

In the art of respiratory masks for supplying breathing gas to a patient, a wide variety of mask configurations are known, including full face masks, masks covering the nose and mouth area and nasal masks, among other variations.

Many prior masks interfere with the user's facial comfort, do not facilitate wearing of eyeglasses, and otherwise have not been well tolerated.

Three areas of common patient complaint are eye, nose bridge and nostril discomfort. For example, masks which interfere with the user's wearing of eyeglasses or which introduce discomfort when used with eyeglasses are less likely to be tolerated by patients who wear eyeglasses. Some prior masks introduce irritating eye leaks, which are flows of breathing gas, either within the mask confines or across the mask seal to the exterior, which pass across the user's eyes and thereby cause irritation.

Nasal masks cover the entire nose area thereby requiring surface pressure around the full perimeter of the nose, including across the bridge area of the nose which, because of the very thin skin there, is readily irritated. Still other gas delivery apparatus such as nasal cannulae can cause irritation within the user's nostrils.

Apart from prior masks per se, the head gear employed in the prior art to retain various sorts of respiratory masks with respect to a user's face have also caused patient discomfort, thus limiting user tolerance. For example, head gear strapping systems which pass over the ears can cause ear tenderness and irritation, and the strapping forces of the head gear required to maintain the larger and heavier of the prior masks in position on a user's face also can cause irritation anywhere they bear against the user's head.

Still further, the strapping forces required to maintain some prior mask seals in sealed engagement with a user's face can be of sufficient magnitude to precipitate irritation and patient intolerance due to the resulting relatively large magnitude strapping forces and the pressure of the mask seal on affected areas of the user's face.

BRIEF SUMMARY OF THE INVENTION

The present invention contemplates a novel and improved nasal mask of minimal size and weight which is especially useful for patients being treated with positive pressure therapy for such conditions as obstructive sleep apnea (OSA). Since the treatment for OSA is applied during sleep, the appliance which interfaces with the patient's respiratory system must be exceptionally light and comfortable, and must accommodate all patient movement occurring during sleep.

The present nasal mask includes a soft, pliable perimeter cushion that contacts a facial area limited essentially to a vertical extent between the tip and lateral flank portions of the user's nose adjacent to the nares and the user's upper lip, and a lateral extent comprising only an area between the cheek portions of the face immediately adjacent to the base of the nose and the upper lip. As such, the mask is very small. The perimeter cushion of the mask cooperates with a balloon seal to form a surface seal on a portion of the user's face within the confines of the limited area characterized above. The cushion disposed between the balloon seal and the mask shell improves patient tolerance by providing for contact or mask retention force distribution anywhere the ballooning action of the primary seal does not carry the mask contact forces.

Owing to its specific size and configuration, the mask avoids the sensitive bridge area of the nose, and no part of it enters the nostrils thereby avoiding the user discomfort associated with physical contact of prior gas delivery apparatus with both of these areas. Further, the low posture of the mask, residing essentially at or below the lowermost extent of the user's nose, reduces the potential for irritating eye leaks and does not interfere with the user's normal field of vision. Further in this regard, the mask allows the user to wear eyeglasses if needed or desired, and the particular headgear structure which forms another aspect of the invention completely avoids ear contact thus permitting eyeglass stems to be worn over the ears in the conventional manner without irritation.

In a further enhancement of the novel mask, exhaust ports are provided to allow exhaled air to escape by blowing away from the user such that the exhalation flow does not result in air flow passing over the user's face, notably the eyes.

The balloon seal of the novel mask includes a thin, textured, elastomeric membrane which forms sealing contact with the small surface area portion of the user's face as characterized above. Due to the high degree of seal flexibility, a high integrity surface seal is maintained with the user's face by even a very small positive pressure within the mask, and with only minimal mask strapping or retention force. The textured surface of the seal membrane further enhances user comfort by allowing a controlled micro leak of breathing gas to pass across the seal interface from the positive pressure environment within the mask to ambient atmosphere. The result is ventilation of the seal interface and an air cushion effect, both of which further enhance user comfort.

These and other aspects of the invention provide a novel and improved apparatus for delivery of breathing gas to a patient.

It is therefore one object of the invention to provide such a novel apparatus for gas delivery to a patient.

A more specific object of the invention is to provide a novel nasal mask and headgear for delivery of breathing gas to a patient.

A still further object of the invention is to provide a novel headgear for use in retaining a patient gas delivery interface with respect to a user's face.

These and other objects and further advantages of the invention will be more readily appreciated upon consideration of the following detailed description and the accompanying drawings, in which.

Figure 1:
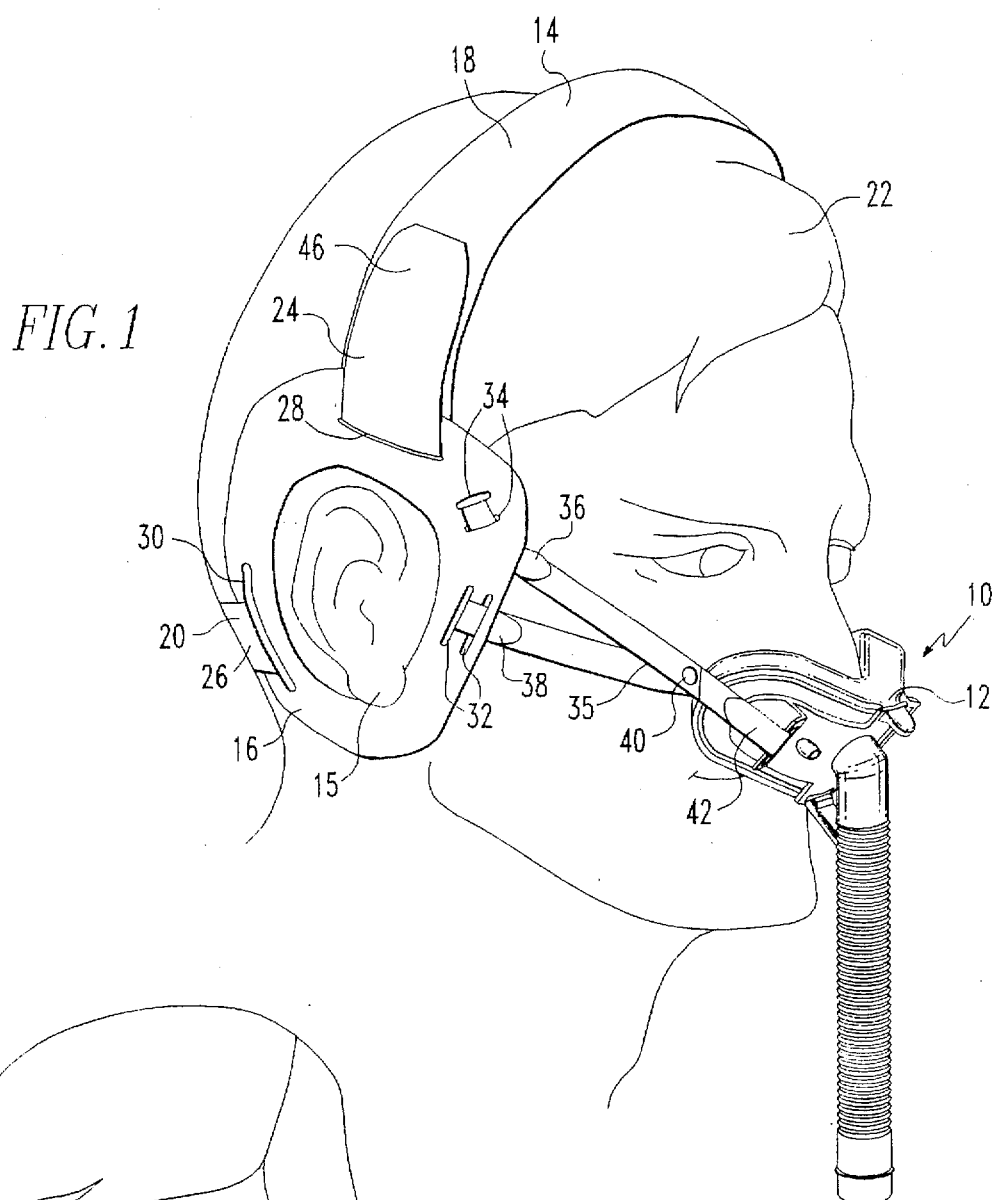
FIG. 1 is a pictorial representation of a user wearing a nasal mask and headgear according to one presently preferred embodiment of the instant invention.

There is generally indicated at 10 in FIG. 1 a nasal mask and headgear apparatus comprised of a mask 12 and retaining headgear 14.

Headgear 14 includes a pair of ear pieces shown as ring elements 16, one encompassing each ear 15 of a user's head 22, and a pair of head bands 18 and 20 which pass about the user's head 22. The band 18 extends over the top of the head and the band 20 extends around the back of the head as shown. The bands 18 and 20 include end portions 24, 26, respectively, having infinitely (i.e., continuously) adjustable attachment means, VELCRO (tm) brand fastener tape 46 for example, by which the bands 18 and 20 are secured with respect to rings 16 after being passed through respective slots 28 and 30 in the rings 16. The slots 28 and 30 are positioned, as shown, to receive and retain the bands extending over the top of the head and around the back of the head.

Figure 2:
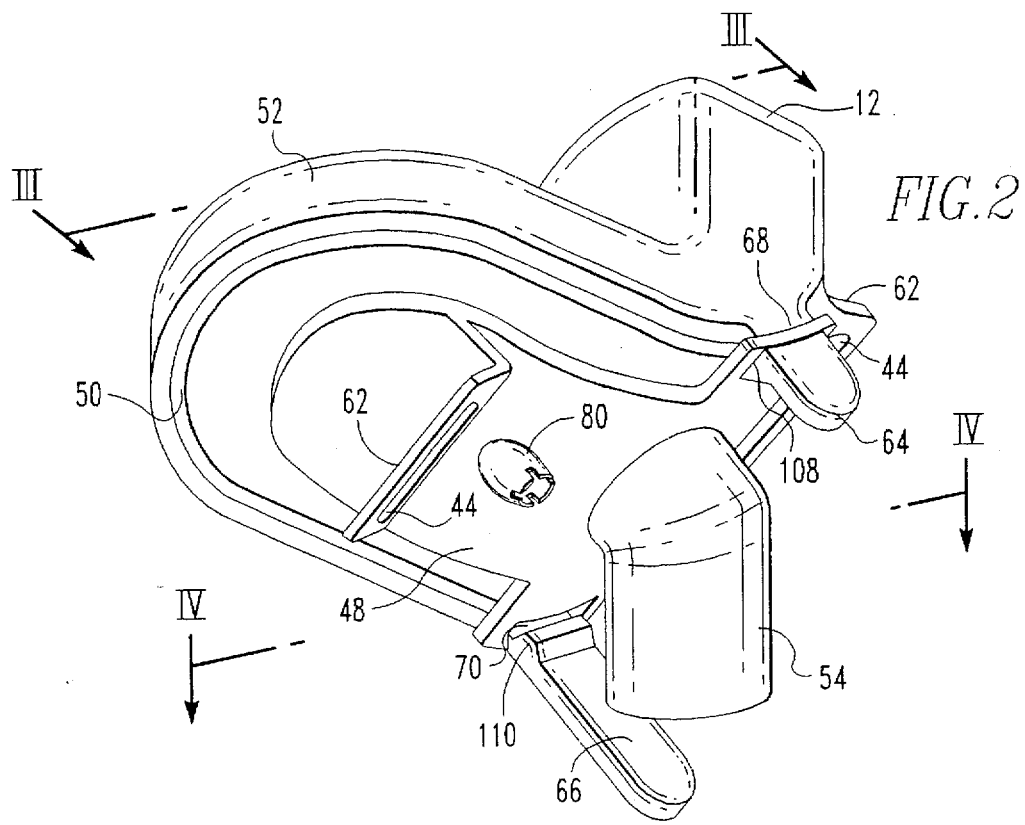
FIG. 2 is an enlarged perspective view of the mask of FIG. 1 with the connecting straps of the headgear not shown.

Each ring 16 additionally includes pairs of slots 32 and 34 for receiving the free ends 36, 38, respectively, of a mask retention strap 35. The strap ends 36 and 38 merge and are secured together at a point 40 located forwardly of ring 16, and from point 40 a free end 42 of the retention strap 35 extends forwardly for attachment to the mask 12 by being passed through apertures or slots 44 of mask 12 (FIG. 2). As with headbands 18 and 20, the strap ends 36, 38 and 42 may be selectively retained and infinitely adjustable as by having attachment means such as VELCRO (tm) brand fastener tape suitably attached to their terminal ends. Alternatively, strap ends 36 and 38 preferably are not provided with such fastening means, but instead are secured by being woven through the pairs of slots 34 and 32 where they are frictionally retained by the slight tension forces necessary to retain the mask 12 with respect to the user's face.

For purposes of structural uniformity and comfort, all strapping materials described above may be suitable elasticized strapping having a loop pile on one side thereof. A suitable length of the hook portion of a hook and loop fastener such as VELCRO (tm) brand fastener tape thus may be secured to the free end of any such strap, as indicated at 46 for example, for engagement with the loop pile side of the strapping material.

The headgear ear pieces 16 are formed preferably from a light weight, flexible plastic material such as Bayer TEXIN 985 polyurethane. The material used for ear pieces 16 is to be sufficiently flexible that the strapping forces allow the ear pieces 16 to conform to the shape of the user's head without otherwise deforming significantly in response to the strapping forces of straps 18, 20 and 35.

Figure 3:
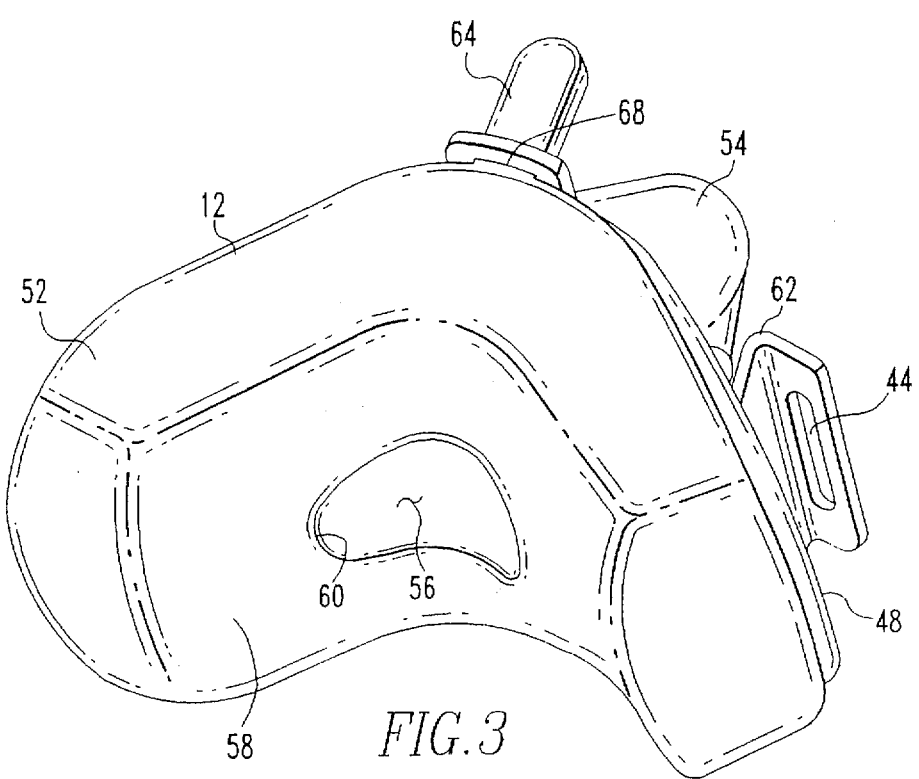
FIG. 3 is a perspective view of the mask of FIG. 2 taken generally from the vantage point of line III—III in FIG. 2.

Referring to FIGS. 2 and 3, mask 12 comprises a generally rigid, formed face plate member 48 which is preferably injection molded from polycarbonate material such as GE LEXAN polycarbonate, a resiliently flexible cushion member 50 which is preferably molded from a thermoplastic or thermosetting elastomer, such as GL5 Kraton G-6705 and a seal 52 which is preferably molded from silicone rubber material, for example Bayer Baysilone LSR 4050.

Figure 4:
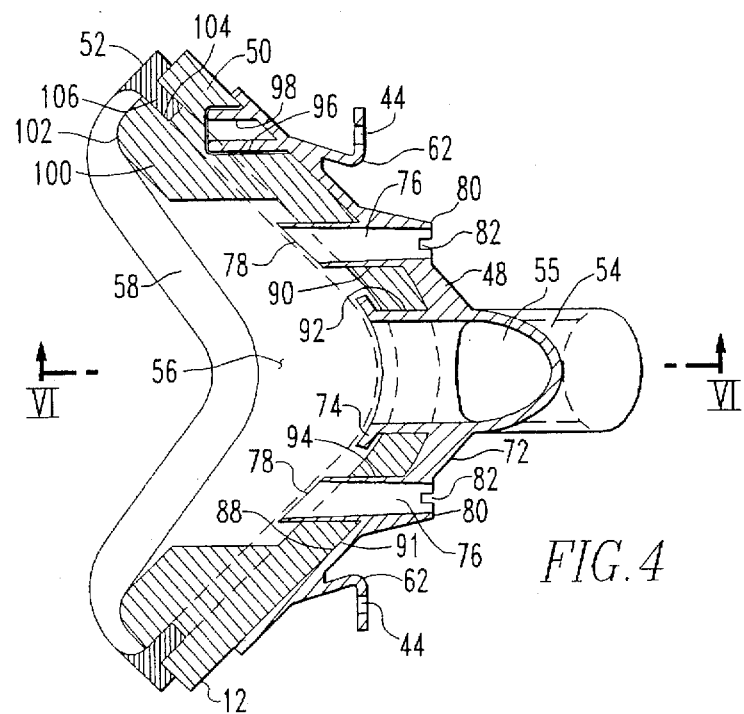
FIG. 4 is a sectional view taken on lines IV—IV of FIG. 2.

As may be generally appreciated from FIGS. 2 to 4, breathing gas is provided via an integral port 54 on face plate 48 into a cavity 56 which is formed by cushion member 50 and enclosed by a flap seal portion 58 of seal 52. A user may breath the gas supplied to cavity 56 through the nostrils via an opening 60 formed in flap seal portion 58 located as so confront the nares of the user.

Other features of the mask structure evident in FIGS. 2 and 3 are projections 62 having the slots 44 to receive and retain strap ends 42, and retention tabs 64 and 66 of seal 52 which cooperate with corresponding retention slots 68 and 70 of face plate 48 to assist in the retention of seal 52 with respect to the mask assembly. A further feature of tabs 64 and 66 is that they are of differing cross sectional configuration, corresponding to differing cross sectional configurations for the slots 68 and 70, whereby the tabs 64 and 66 provide for non-redundant positioning and assembly of the seal 52 with respect to the face plate 48.

Also shown in FIGS. 2 and 3 is the generally V-shaped configuration of the mask 12 which opens or diverges generally in an anterior to posterior direction when positioned in confronting relationship with a user's nose and upper lip, thus generally conforming to the anatomical structure of these portions of the user's face. This also allows the mask seal to more readily conform with and seal against the user's face within the area of mask contact shown in FIG. 9.

Figure 5:
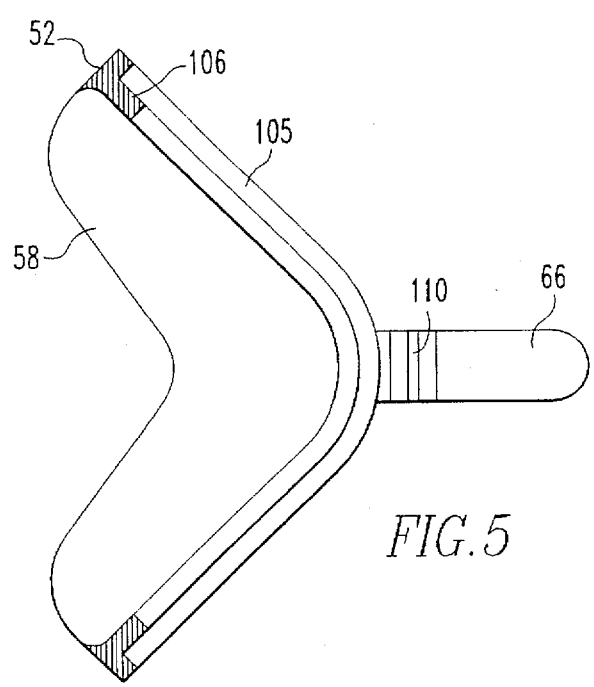
FIG. 5 is a sectional view of the seal portion of the mask shown in FIG. 4.
Figure 6:
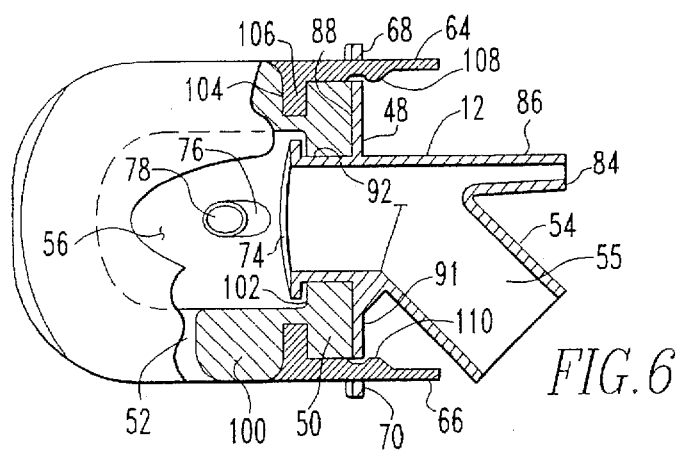
FIG. 6 is a sectional view taken on lines VI—VI of FIG. 4.
Figure 7:
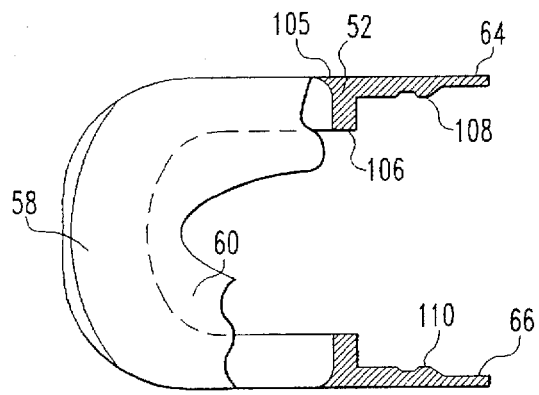
FIG. 7 is a sectional view of the seal portion of the mask shown in FIG. 6.
Figure 8:
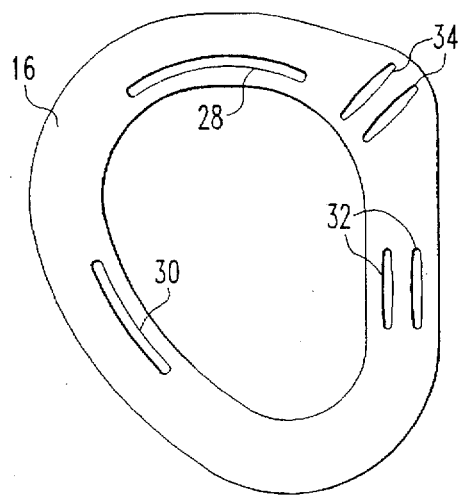
FIG. 8 is a side elevation of an ear ring portion of the mask headgear shown in FIG. 1.

Further details of the mask assembly 12 are shown in FIGS. 4 and 6, with details of the seal 52 shown separately in FIGS. 5 and 7. Referring first to FIGS. 4 and 6, face plate 48 includes a rigid, generally V-shaped body member 72 having the port 54 formed integrally therewith and extending inwardly of the face plate body 72 to form an inwardly projecting, flanged inner open end 74. Laterally outward to either side of port 54 there are formed openings 76 which project inwardly of body 72 to open inner ends 78, and which additionally open outwardly on the opposed side of the body 72 at outer open ends 80. The outer open ends 80 may be slotted or otherwise formed as indicated at 82 to increase the open area at the outer ends 80 and reduce the possibility of inadvertent closure such as might occur upon movements of a user in sleep.

A further structural feature of face plate 48 may be a control opening 84 formed in an extension 86, the opening 84 communicating with the interior 55 of port 54 for such purposes as connection to a desired monitoring device such as a pressure monitoring device, or to a supplemental oxygen source.

Face plate body 72 further includes an inner surface 88 which receives the elastomeric cushion member 50 adjacent thereto. Accordingly, the cushion member 50 also is of generally V-shaped form, having a surface 91 which resides adjacent to and conforms with the surface 88 to form an assembly with face plate 48.

The inner open ends 78 of openings 76, and the inner flanged end 74 of port 54 project through cushion member 50, which has corresponding through openings 90, 92 and 94 to receive the same. In addition, a blind opening 96 is formed in cushion member 50 to receive an inward projection 98 of face plate body 72 in order to ensure correct assembly of cushion member 50 to face plate 48.

A peripheral portion 100 of cushion member 50 surrounds and partially forms the cavity 56, into which port 55 opens. The cushion member peripheral portion 100 is of sufficient section thickness to provide a structural mass within which a peripheral groove 104 is formed to receive a corresponding flange portion 106 of seal 52 for retention of the seal 52 with respect to cushion member 50.

The seal 52 need not be otherwise retained with respect to the mask assembly, although additional retention may be provided by tabs 64 and 66 passing through and engaged within respective slot 68 and 70 as above described. More specifically, each of tabs 64 and 66 includes a transverse ridge portion 108, 110, and the corresponding transverse portion of the respective tabs 64 and 66 thus is of a greater section thickness than the width of the respective slots 68 and 70. As the slots 68 and 70 are formed in the rigid material of face plate 48 whereas the tabs 64 and 66 are integrally formed with seal 52 from elastically deformable material, pulling the tabs 64 and 66 through the respective slots 68 and 70 will sufficiently deform the ridged portions 108 and 110 to force them through the respective slots 68 and 70. As seal 52 overlies and generally encloses cushion member 50, the engagement of tabs 66 and 68 in the respective slots of face plate member 48 as above described also serves to retain cushion member 50 in the mask assembly.

Referring to FIGS. 5 and 7, the seal 52 may have a base portion 105, including flange portion 106 and tabs 64 and 66, formed from a material such as that specified for cushion member 50. The textured flap seal portion 58 is preferably formed from the specified silicone rubber material either integrally with base portion 105 or is suitably affixed thereto as by adhesive bonding to form the seal 52. The flap seal portion 58 of seal 52 is a very thin section, flappable, flexible seal membrane which is capable of conforming precisely to variations in the surface profile of the user's face in the contact area under only minimal inflation pressure. For example, the flap seal 58 may be an expanse of silicone rubber as described with a section thickness of 0.010+0.003 inches.

Figure 9:
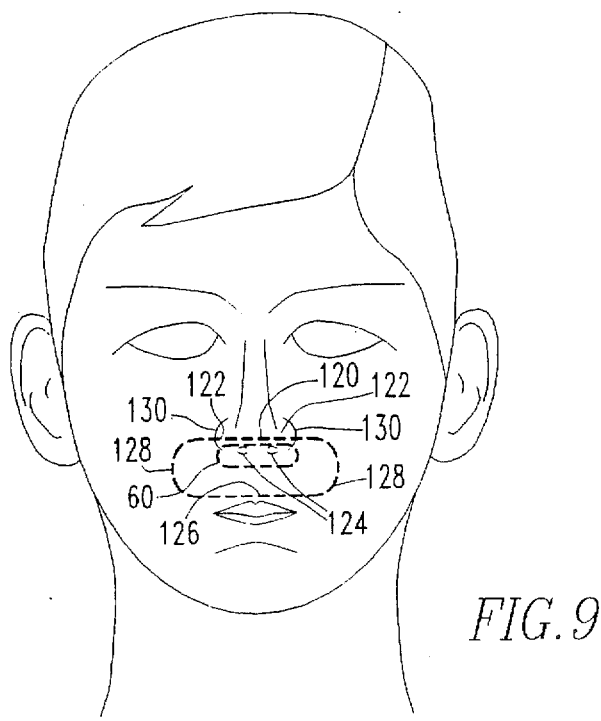
FIG. 9 is a frontal view of a user's face showing the area covered by the novel mask.

In use, the mask and headgear assembly is placed in position on a user's face and head as shown in FIG. 1 and straps 18 and 20 are adjusted for a suitable fit of ear pieces 16 on the user's head. Straps 35 are then adjusted to position and retain mask 12, with seal 52 inflated by gas pressure within cavity 56 to achieve sealing engagement with a portion of the user's face within the confines of the area between the lower part of the user's nose and the upper lip, as described hereinabove and as shown in FIG. 9, and with opening 60 confronting the nares of the user. Specifically, the mask seal contact area, including contact by an outer surface 102 of the perimeter portion 100 of cushion member 50, is limited to the facial area essentially defined as a vertical extent having the tip 120 and immediately adjacent lateral flanks 122 of the user's nose adjacent to the nares 124 as its upper extremity, and the user's upper lip 126 as its lower extremity, and a lateral extent having the cheek portions 128 of the user's face laterally adjacent to both the base 130 of the nose and the upper lip 126 as its lateral extremities.

In this configuration, this very light weight mask provides breathing gas to the nares of the user under positive pressure with only minimal strapping or retention force and very limited mask contact forces on the face. The mask thus avoids such irritants as superficial irritation to the ears and nose bridge, interference with the wearing of eyeglasses, disturbing gas leaks passing across the face and/or the eyes, interference with the visual field of the user, and excess mask weight, bulk or size. With amelioration of all of these potential problems, a user will more readily tolerate the mask, and the gas therapy supplied via the mask thus may be better tolerated and more effective.

Figure 10:
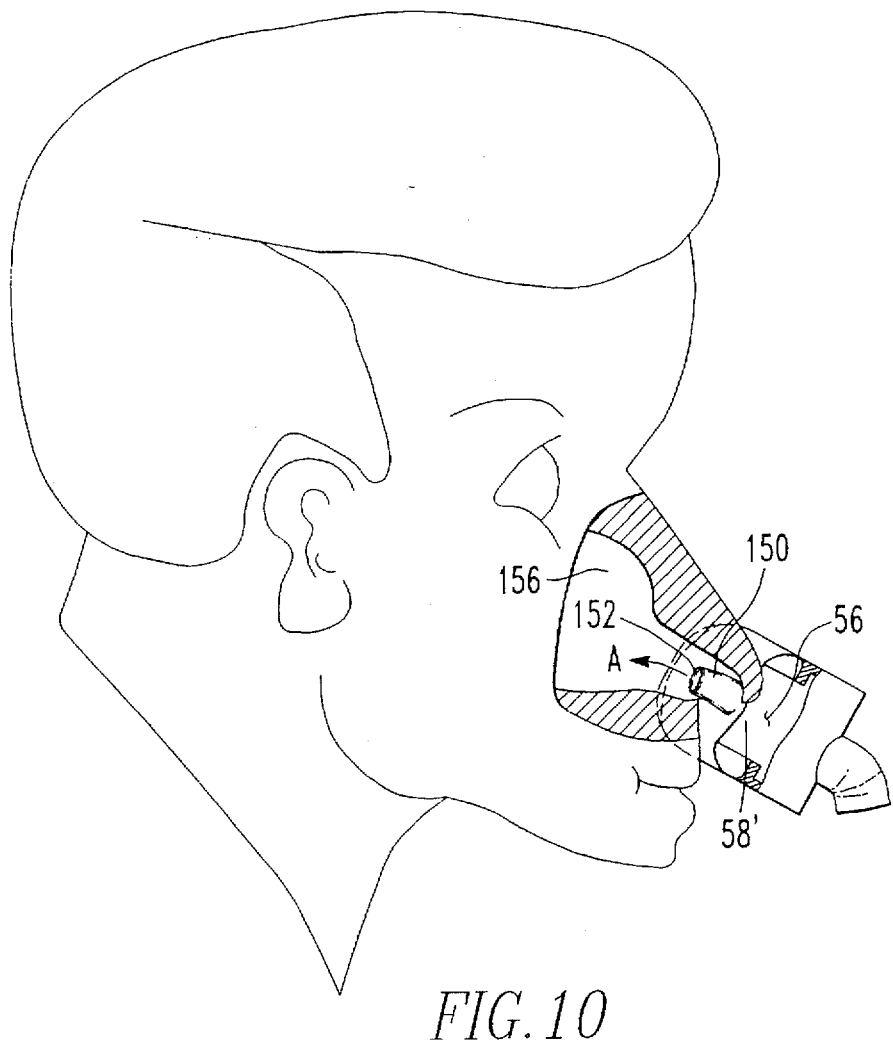
FIG. 10 shows an alternative embodiment of the invention.
Figure 11:
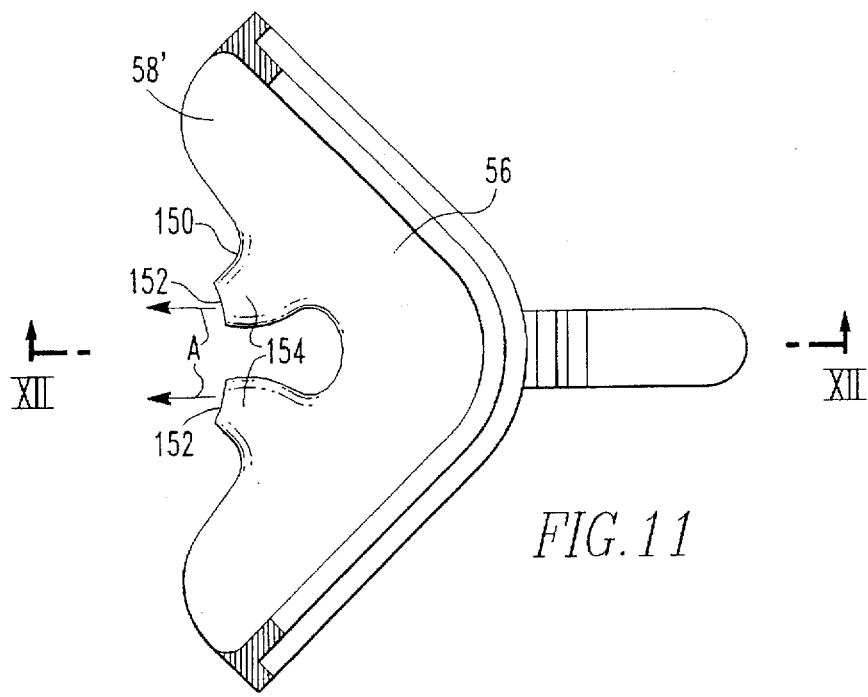
FIG. 11 is a sectional view, similar to FIG. 5, of the embodiment of FIG. 10.
Figure 12:
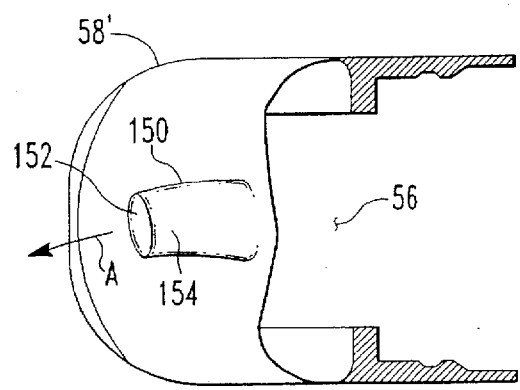
FIG. 12 is a sectional view taken on line XII—XII of FIG. 11.

In an alternative embodiment of the invention, as shown in FIGS. 10–12, the mask includes a modified flap seal portion 58' with improved nasal cannulae 150 formed integrally therewith in lieu of the opening 60 as shown in FIG. 3. The cannulae 150 communicate with space 56 to provide breathing gas via openings 152 through the cannulae 150 as indicated by arrows A.

Prior, known nasal cannulae direct air flow upwardly into the nose in a direction generally perpendicular to the nares, which are not perpendicular to the nasal passages. More particularly, as shown in FIG. 10 the nasal passages 156 extend generally in a direction from the nares toward the back of the head. Further, known prior cannulae have had very small diameter exit openings which increase the gas flow velocity where it enters the nose. Prior cannulae thus often have caused a sensation of air jetting and of drying in the nasal passages due to the higher than necessary gas flow velocity and the gas flow generally not being directed in an anterior to posterior direction.

The improved mask seal structure of FIGS. 10–12 includes nasal cannulae body portions 154 integrally formed with flap seal portion 58', preferably from the same material as above specified for flap seal portion 58. Cannulae body portions 154 are formed with respect to seal 58' such that when the mask is worn in the manner as above described, the cannulae bodies 154 project into the nares of the user in a generally anterior to posterior direction as shown in FIG. 10, whereby the gas flow emerging from the open ends 152 of cannulae bodies 154 is directed in the same direction, that is, toward the back of the user's head. An enlarged opening 152 is utilized to avoid unnecessarily increasing the gas flow velocity at the cannulae openings 152. The cannulae bodies 154 are further formed to support the nares open, and to provide an aerodynamically efficient gas flow passage which directs the gas flow as above described. This helps to minimize the sensation of air jetting, that is, the sensation of gas flowing within the nasal passages, and in addition minimizes the sensation of nasal passageway dryness.

In particular, the cannulae bodies 154 are aerodynamically formed to modify the velocity and flow pattern of gas passing therethrough such that the gas flow emerging from the openings 152 is correctly directed in the above described anterior to posterior direction toward the back of the user's head. This is distinct from prior nasal cannulae which generally have been characterized by short length of straight tubing that neither supports the nares open nor modifies or directs the gas flow. Further, prior cannulae typically are positioned to direct gas flow upwardly into the nares in a direction generally perpendicular to the nares rather than in an anterior to posterior direction.

In accordance with the description hereinabove, we have invented a novel and improved respiratory mask for delivery of breathing gas to a user through the nares. Of course, we have envisioned various alternative and modified embodiments of the invention, and surely such would also occur to others versed in the art once they were apprised of our invention. Accordingly, it is our intention that the invention should be construed broadly and limited only by the scope of the claims appended hereto.

We claim:

1. A respiratory mask for engaging a user's face to provide an interface for nasal delivery of breathing gas to the user, said mask comprising:

a mask assembly;

said mask assembly including a seal means which is engagable with a user's face to provide a sealed interface therewith only within a sealing area surrounding the nares of the user;

said seal means including a flexible seal which forms a chamber surrounding the nares of the user of containing gas pressure and to permit the gas pressure to support said flexible seal and engage said flexible seal in sealing engagement with the user's face;

gas inlet means for conveying breathing gas into said chamber for delivery of the breathing gas to the nares of the user and to support said flexible seal; and said mask assembly being of a form that said sealing area is bounded at its upper extremity by the lower end of the user's nose including the tip and lateral flanks thereof, and at its lower extremity by the user's upper lip.

2. The mask as set forth in claim 1 wherein said sealing area is further bounded at its lateral extremities by respective left and right facial areas vertically intermediate and laterally adjacent to said upper and lower extremities.

3. The mask as set forth in claim 1 wherein said flexible mask assembly includes a peripheral cushion means formed such that said cushion means confronts the user's face only at peripheral portions of said sealing area.

4. The mask as set forth in claim 3 wherein said seal means includes flap means overlying and extending inwardly of said peripheral cushion means for engagement with the user's face within the confines of said sealing area.

5. A nasal respiratory mask assembly adapted for delivering breathing gas to the nares of a user comprising:

a rigid face plate;

a resilient cushion means carried by said face plate;

said cushion means including a peripheral cushion portion with seal retaining means and a chamber portion disposed within the confines of said peripheral cushion portion for confronting relation with the nares of the user;

said cushion means further including aperture means communicating with said chamber portion and said face plate including port means opening through said aperture means for delivery of breathing gas to said chamber portion;

flexible seal means engaging said seal retaining means in releasable, sealed engagement therewith for containing gas pressure within said chamber portion to permit support of said flexible seal means by the gas pressure;

said flexible seal means overlying said chamber portion and including an opening means;

said flexible seal means being adapted for sealed engagement only with a sealing area corresponding to that portion of the user's face surrounding the nares of the user, with said opening means communicating with the nares of the user to permit delivery of breathing gas from said chamber portion to the user; and said sealing area being bounded at its upper extremity by the lower end of the user's nose including the tip and lateral flanks thereof, and at its lower extremity by the user's upper lip.

6. The respiratory mask assembly as set forth in claim 5 wherein said flexible seal means includes peripheral flange means and said seal retaining means includes groove means formed in said peripheral cushion portion to cooperably receive said flange means for sealing engagement therebetween and to retain said seal means with respect to said cushion means.

7. The mask assembly as set forth in claim 6 wherein said flexible seal means additionally includes elongated tab means and said face plate includes tab receiving aperture means for receiving said tab means to retain said seal means with respect to said face plate with said cushion means disposed generally intermediate said seal means and said face plate.

8. The mask assembly as set forth in claim 5 wherein said opening means includes cannulae means formed to direct breathing gas flow into the nares of the user in an anterior to posterior direction with respect to the head of the user.

9. A head gear adapted to be worn by a user for retaining a respiratory appliance with respect to the face of the user comprising:

load bearing ear piece means adapted to engage a side portion of the user's head in fully surrounding relationship with the corresponding ear of the user;

head strap means connected to said ear piece means and adapted to pass about the head of the user without engaging the user's ears; and retention strap means connected to said ear piece means and adapted to be connected to such a respiratory appliance for retaining such a respiratory appliance with respect to the face of the user without said retention strap means engaging the user's ear.

10. The head gear as set forth in claim 9 wherein said ear piece means includes a pair of, load bearing closed loop means each adapted to completely surround one of the user's ears.

* * * * *

UNITED STATES PATENT AND TRADEMARK OFFICE
CERTIFICATE OF CORRECTION

PATENT NO. : 5,724,965
DATED : March 10, 1998
INVENTOR(S) : P. M. Handke, et al

It is certified that error appears in the above—identified patent and that said Letters Patent is hereby corrected as shown below:

In patent claim 3, line 1, delete "flexible", and in line 3 delete "only".

In patent claim 4, insert -- flexible -- in line 1 directly after "said" and in line 4 insert -- only -- directly after "face".

Signed and Sealed this

Seventh Day of July, 1998

Attest:

BRUCE LEHMAN

Attesting Officer

Commissioner of Patents and Trademarks